United States Patent
Nicholson et al.

(10) Patent No.: US 11,129,550 B2
(45) Date of Patent: Sep. 28, 2021

(54) THRESHOLD RANGE BASED ON ACTIVITY LEVEL

(71) Applicant: Lenovo (Singapore) Pte. Ltd., Singapore (SG)

(72) Inventors: John Weldon Nicholson, Cary, NC (US); Daryl Cromer, Raleigh, NC (US)

(73) Assignee: Lenovo (Singapore) Pte. Ltd., Singapore (SG)

( * ) Notice: Subject to any disclaimer, the term of this patent is extended or adjusted under 35 U.S.C. 154(b) by 655 days.

(21) Appl. No.: 15/938,649

(22) Filed: Mar. 28, 2018

(65) Prior Publication Data

US 2019/0298230 A1    Oct. 3, 2019

(51) Int. Cl.

| A61B 5/0205 | (2006.01) |
| A61B 5/024 | (2006.01) |
| A61B 5/021 | (2006.01) |
| A61B 5/11 | (2006.01) |
| A61B 5/145 | (2006.01) |
| A61B 5/00 | (2006.01) |
| A61B 5/08 | (2006.01) |

(52) U.S. Cl.
CPC .......... *A61B 5/1118* (2013.01); *A61B 5/0205* (2013.01); *A61B 5/14532* (2013.01); *A61B 5/7246* (2013.01); *A61B 5/7275* (2013.01); *A61B 5/746* (2013.01); *A61B 5/021* (2013.01); *A61B 5/024* (2013.01); *A61B 5/0816* (2013.01); *A61B 5/747* (2013.01)

(58) Field of Classification Search
CPC . A61B 5/1118; A61B 5/0205; A61B 5/14532; A61B 5/7246; A61B 5/7275; A61B 5/746; A61B 5/021; A61B 5/024; A61B 5/0816; A61B 5/747
USPC .................................................. 600/365–366
See application file for complete search history.

(56) References Cited

U.S. PATENT DOCUMENTS

| 8,005,524 | B2 * | 8/2011 | Brauker | A61B 5/726 600/345 |
| 8,160,669 | B2 * | 4/2012 | Brauker | A61B 5/14532 600/347 |
| 8,216,139 | B2 * | 7/2012 | Brauker | A61B 5/7275 600/365 |
| 8,251,906 | B2 * | 8/2012 | Brauker | A61B 5/14865 600/365 |
| 8,257,259 | B2 * | 9/2012 | Brauker | A61M 5/1723 600/365 |
| 8,265,725 | B2 * | 9/2012 | Brauker | A61B 5/7455 600/345 |
| 8,282,549 | B2 * | 10/2012 | Brauker | A61B 5/145 600/365 |

(Continued)

*Primary Examiner* — Navin Natnithithadha
(74) *Attorney, Agent, or Firm* — Ference & Associates LLC

(57) ABSTRACT

One embodiment provides a method, including: obtaining, at an information handling device, at least one physiological data point that corresponds to a physiological metric associated with a user; determining, using a processor, an activity type of the user; determining, using a processor, whether the at least one physiological data point is outside a threshold range for the physiological metric based on the activity type; and providing, responsive to determining that the at least one physiological data point is outside the threshold range, a notification. Other aspects are described and claimed.

18 Claims, 3 Drawing Sheets

(56) References Cited

U.S. PATENT DOCUMENTS

| | | | | |
|---|---|---|---|---|
| 8,290,561 B2* | 10/2012 | Brauker | A61B 5/7257 600/345 |
| 8,374,667 B2* | 2/2013 | Brauker | A61B 5/14865 600/345 |
| 8,469,886 B2* | 6/2013 | Brauker | A61B 5/7275 600/365 |
| 8,597,274 B2* | 12/2013 | Sloan | A61B 5/14532 604/504 |
| 8,657,745 B2* | 2/2014 | Brauker | A61B 5/1451 600/365 |
| 8,747,315 B2* | 6/2014 | Brauker | A61B 5/7475 600/365 |
| 8,801,610 B2* | 8/2014 | Brauker | A61B 5/7264 600/365 |
| 2005/0203360 A1* | 9/2005 | Brauker | A61B 5/7275 600/345 |
| 2008/0306435 A1* | 12/2008 | Kamath | A61B 5/0002 604/66 |
| 2008/0306444 A1* | 12/2008 | Brister | A61B 5/14546 604/131 |
| 2009/0036758 A1* | 2/2009 | Brauker | A61B 5/7275 600/309 |
| 2009/0043181 A1* | 2/2009 | Brauker | A61B 5/7257 600/347 |
| 2009/0043182 A1* | 2/2009 | Brauker | A61M 5/1723 600/347 |
| 2009/0043525 A1* | 2/2009 | Brauker | A61B 5/1468 702/104 |
| 2009/0043541 A1* | 2/2009 | Brauker | A61B 5/14865 702/189 |
| 2009/0043542 A1* | 2/2009 | Brauker | A61B 5/14532 702/189 |
| 2009/0062635 A1* | 3/2009 | Brauker | A61M 5/1723 600/365 |
| 2009/0203981 A1* | 8/2009 | Brauker | A61B 5/14865 600/365 |
| 2009/0204341 A1* | 8/2009 | Brauker | A61B 5/14503 702/19 |
| 2009/0299162 A1* | 12/2009 | Brauker | A61B 5/742 600/365 |
| 2010/0010324 A1* | 1/2010 | Brauker | A61B 5/746 600/309 |
| 2010/0010331 A1* | 1/2010 | Brauker | A61B 5/7275 600/365 |
| 2010/0010332 A1* | 1/2010 | Brauker | A61B 5/7275 600/365 |
| 2010/0016687 A1* | 1/2010 | Brauker | A61B 5/726 600/309 |
| 2010/0022855 A1* | 1/2010 | Brauker | A61B 5/7264 600/309 |
| 2010/0030038 A1* | 2/2010 | Brauker | A61B 5/1486 600/309 |
| 2010/0030484 A1* | 2/2010 | Brauker | A61B 5/1495 702/19 |
| 2010/0030485 A1* | 2/2010 | Brauker | A61B 5/14503 702/19 |
| 2010/0045465 A1* | 2/2010 | Brauker | A61B 5/1468 340/573.1 |
| 2010/0179400 A1* | 7/2010 | Brauker | A61B 5/1486 600/309 |
| 2010/0295686 A1* | 11/2010 | Sloan | A61B 5/746 340/573.1 |
| 2010/0298685 A1* | 11/2010 | Hayter | A61M 5/1723 600/365 |
| 2010/0298765 A1* | 11/2010 | Budiman | A61B 5/4839 604/66 |

* cited by examiner

THRESHOLD RANGE BASED ON ACTIVITY LEVEL

BACKGROUND

Information handling devices ("devices"), for example wearable devices (e.g., fitness/activity trackers, smart watches, etc.), smart phones, tablet devices, and the like, may be capable of monitoring various health related data points. For example, devices may be able to monitor physiological aspects (e.g., heart rate, blood pressure, glucose levels, etc.) and/or track other fitness-related metrics (e.g., distance walked or run, activity currently engaged in, calorie consumption, etc.) associated with a user. Some devices may also provide notifications or alerts if the health related data points are above or below a predetermined threshold.

BRIEF SUMMARY

In summary, one aspect provides a method, comprising: obtaining, at an information handling device, at least one physiological data point that corresponds to a physiological metric associated with a user; determining, using a processor, an activity type of the user; determining, using a processor, whether the at least one physiological data point is outside a threshold range for the physiological metric based on the activity type; and providing, responsive to determining that the at least one physiological data point is outside the threshold range, a notification.

Another aspect provides an information handling device, comprising: a processor; a memory device that stores instructions executable by the processor to: obtain at least one physiological data point that corresponds to a physiological metric associated with a user; determine an activity type of the user; determine whether the at least one physiological data point is outside a threshold range for the physiological metric based on the activity type; and provide, responsive to determining that the at least one physiological data point is outside the threshold range, a notification.

A further aspect provides a product, comprising: a storage device that stores code, the code being executable by a processor and comprising: code that obtains at least one physiological data point that corresponds to a physiological metric associated with a user; code that determines an activity type of the user; code that determines whether the at least one physiological data point is outside a threshold range for the physiological metric based on the activity type; and code that provides, responsive to determining that the at least one physiological data point is outside the threshold range, a notification.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
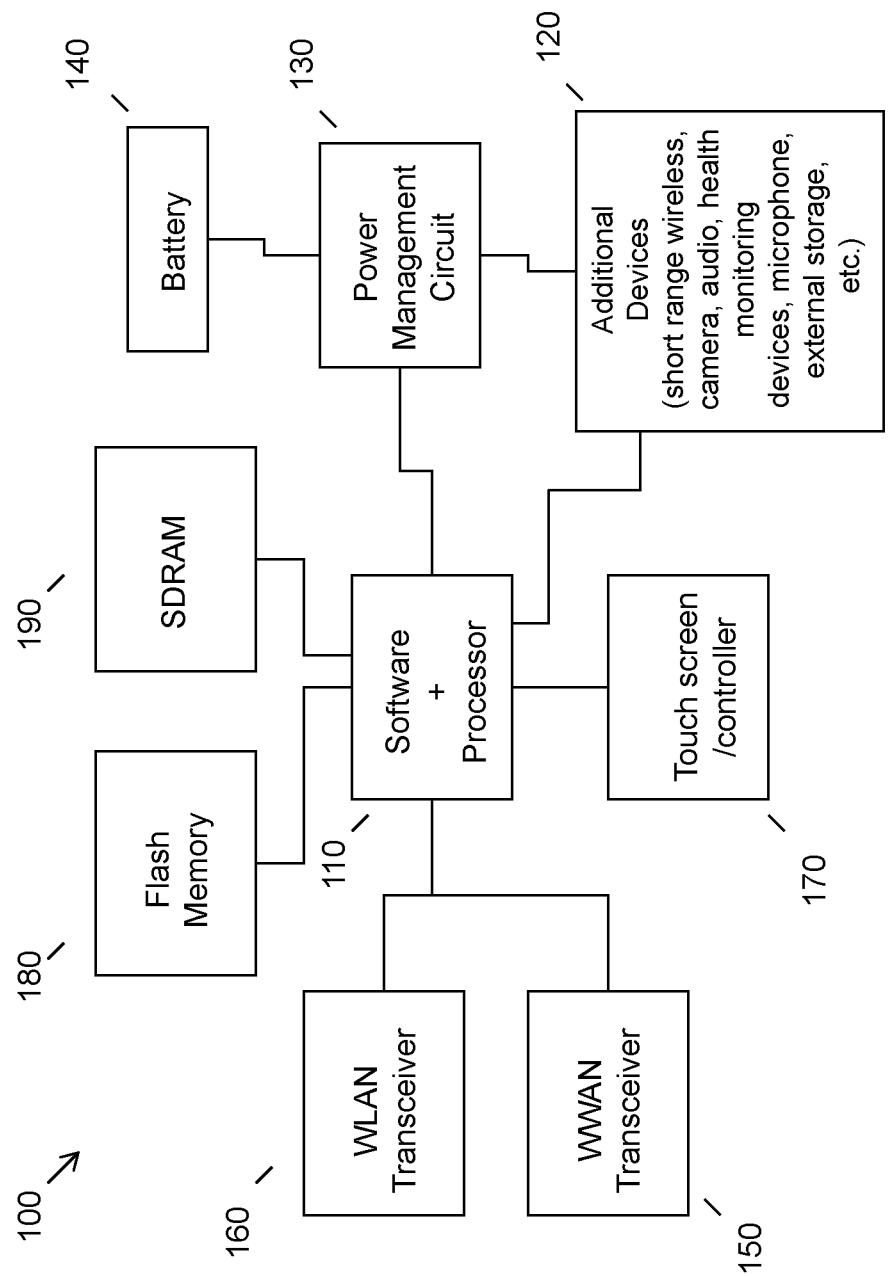
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Devices capable of monitoring health and fitness data ("devices") are becoming ever prevalent in society. Generally, these devices monitor and log various health and activity-based metrics of a user throughout the day. Users may access and view this data (e.g., on a display screen of their device, etc.), which may motivate them, for example, to either engage in additional physical activity or refrain from consuming additional calories. Additionally, many individuals rely on these devices to notify them when a health or fitness metric is outside a "normal" range or has exceeded or fallen below a predetermined threshold. For example, a notification may be provided to a user if their measured heart-rate is too high, if their daily step count is too low, etc.

However, conventional methods for providing health-based notifications are static and do not factor in a user's contextual activity before providing the notification. Stated differently, conventional methods simply provide a notification responsive to identifying that a certain metric is above or below a predetermined threshold but do not consider that the threshold may change based on an activity a user is currently engaged in. For example, the typical max peak heart-rate during exercise is 220 beats per minute ("BPM"), whereas the typical heart-rate at rest is about 60 to 100 BPM (40 to 60 BPM for well-trained athletes). The activity level and/or activity type is key in determining whether the measured heart-rate is cause for concern. For instance, it may be perfectly acceptable to have a measured heart-rate of 150 BPM while engaging in rigorous exercise but that same heart-rate during a stagnant activity (e.g., sleeping, sitting watching TV, etc.) may be indicative of a serious condition.

Accordingly, an embodiment provides a method for providing a notification responsive to identifying that at least one physiological data point of a user falls outside of a predetermined threshold range of a corresponding physiological metric based on an activity a user is currently engaged in. In an embodiment, at least one physiological data point corresponding to a physiological metric (e.g., user's heart rate, blood pressure, respiration level, blood glucose level, etc.) associated with a user may be obtained. An embodiment may also determine an activity currently engaged in by the user in order to identify an appropriate threshold range for physiological data points during the activity. An embodiment may thereafter determine whether the obtained physiological data point is outside of a threshold range for the physiological metric based on the activity and provide, responsive to determining that the physiological data point falls outside of the threshold range, a notification (e.g., a notification to a user, a notification to a healthcare professional, etc.). Such a method may enable a user to receive more context accurate notifications and/or alerts related to their current health condition.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera, audio capture device such as a microphone, a thermal sensor, etc. System 100 often includes a touch screen 170 for data input and display/rendering. System 100 also typically includes various memory devices, for example flash memory 180 and SDRAM 190.

Figure 2:
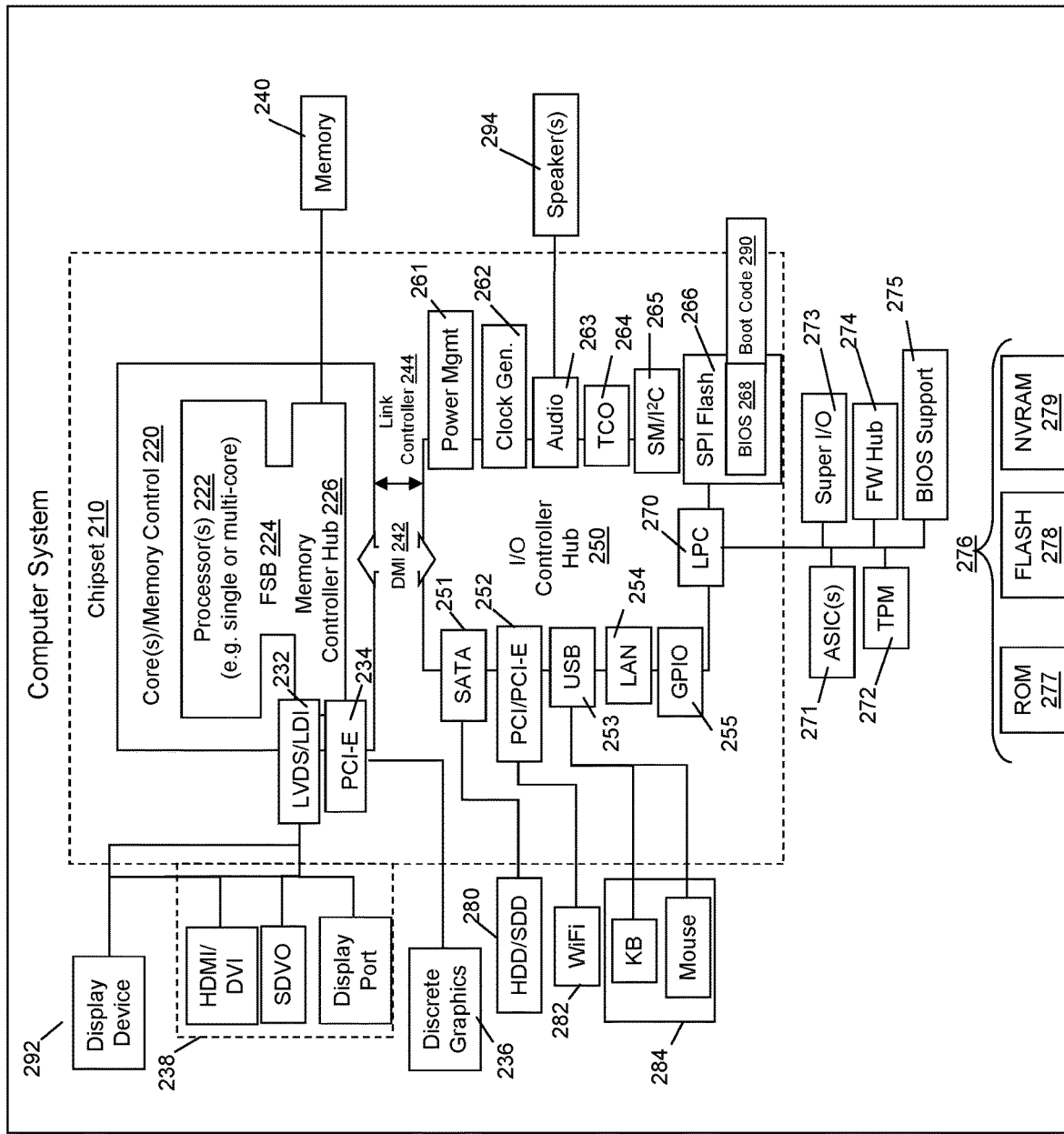
FIG. 2 illustrates another example of information handling device circuitry.

FIG. 2 depicts a block diagram of another example of information handling device circuits, circuitry or components. The example depicted in FIG. 2 may correspond to computing systems such as the THINKPAD series of personal computers sold by Lenovo (US) Inc. of Morrisville, N.C., or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as smart phones, smart watches, fitness trackers, other wearable devices, other health monitoring devices, personal computer devices generally, and/or electronic devices which may monitor and record a user's health and/or fitness data. For example, the circuitry outlined in FIG. 1 may be implemented in a tablet or smart phone embodiment, whereas the circuitry outlined in FIG. 2 may be implemented in a personal computer embodiment.

Figure 3:
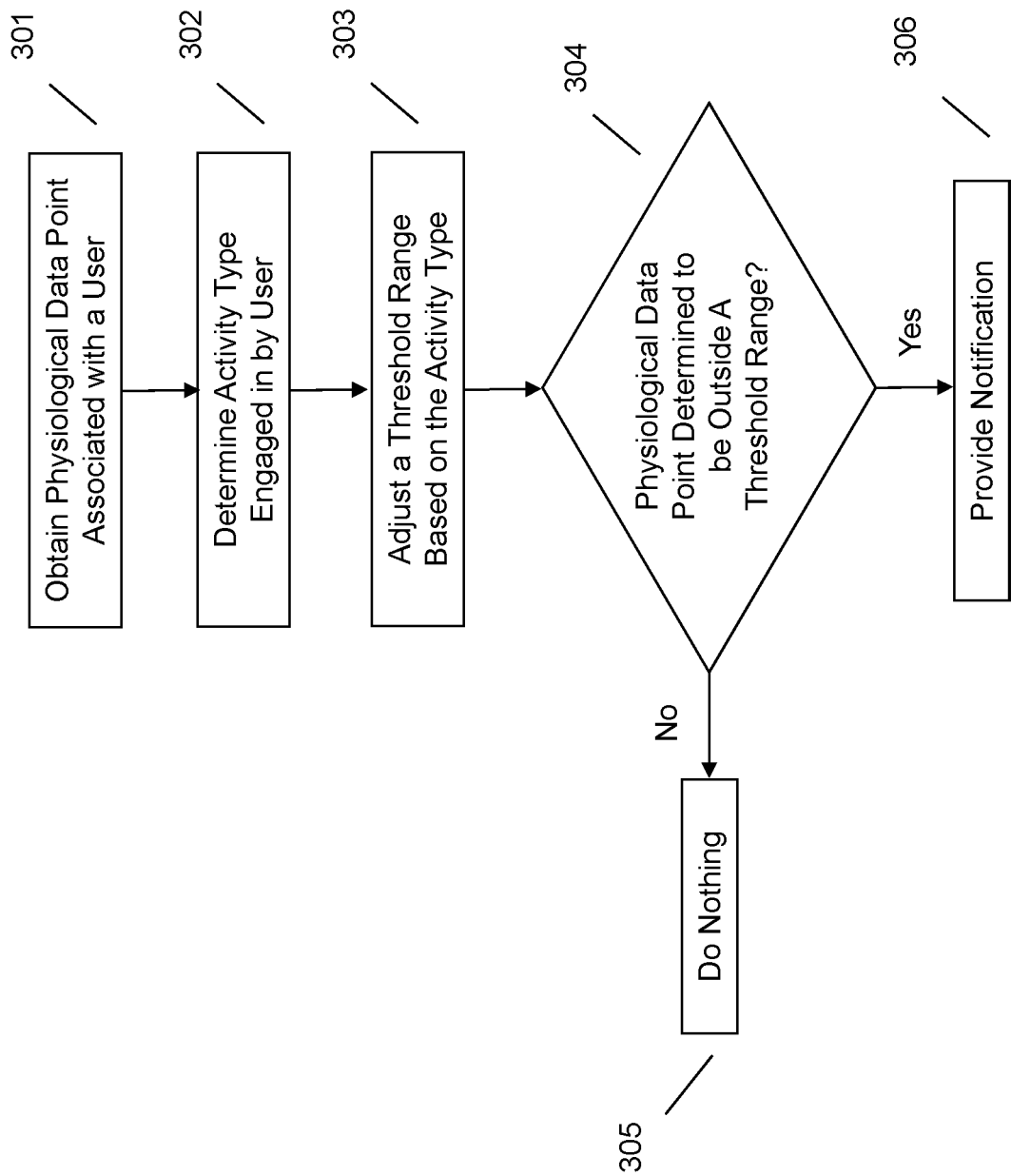
FIG. 3 illustrates an example method of providing a notification responsive to determining that a physiological data point exceeds a predetermined threshold for an activity.

Referring now to FIG. 3, an embodiment may provide a notification to a user that a physiological data point may be outside of a threshold range for an identified activity a user is engaging in. At 301, an embodiment may obtain at least one physiological data point associated with a user using at least one health-tracking device (e.g., smart phone, smart watch, fitness tracker, heart-rate monitor, glucose meter, etc.). In an embodiment, the physiological data point may correspond to one of a variety of different physiological metrics such as a user's heart rate, blood pressure, respiration level, blood glucose level, and the like. In an embodiment, the physiological data point may correspond to a data point at a particular point in time. For example, at time X a user's heart rate is 100 BPM, where 100 BPM may be the physiological data point. An embodiment may obtain the physiological data point using one or more techniques known in the art. An embodiment may continuously obtain physiological data point or, alternatively, may obtain the physiological data points at predetermined intervals.

At 302, an embodiment may determine an activity type associated with a user. In the context of this application, an activity type may refer to an activity (e.g., stagnant activity, active activity, etc.) that a user is engaging in. The activity may be a generic activity (e.g., sleeping, sitting, walking, running, etc.) or a specific activity (e.g., watching TV while sitting, lifting weights in the gym, playing tennis, etc.).

In an embodiment, context data may be received and used to determine the activity type. In an embodiment, the context data may be one or more types of data such as location data, movement data, communication data, social media data, food-consumption data, physiological micro-event data, and the like. For example, a walking user wearing a smart watch may generate movement data (e.g., accelerometer data, gyroscope data, etc.) that an embodiment may receive. An embodiment may thereafter identify (e.g., by comparing the received data to an accessible list of data patterns known to be associated/correlated with specific activity types, etc.) that the received data corresponds to a walking activity type.

In an embodiment, a combination of context data types may be utilized to determine an activity type. The utilization of two or more context data types may provide greater confidence to the system in its activity type determination. Additionally, the utilization of two or more context data types may allow a system to identify a specific activity a user is engaging in. For example, an embodiment may access a user's calendar data to identify that a user has blocked off a one hour period for "Tennis" between the hours of 5 pm-6 pm. Additionally, an embodiment may receive location data (e.g., using GPS data, wireless connection data, etc.) that identifies that the user is at a local tennis court at 5 pm. When an embodiment receives movement data (e.g., from a device worn by the user, etc.) between the hours of 5 pm-6 pm, an embodiment may more confidently associate and/or identify that the movement data corresponds to a Tennis activity.

At 303, an embodiment may adjust a threshold range for a physiological metric based on the determined activity type. An embodiment may thereafter determine, at 304, whether at least one physiological data point falls outside of a predetermined threshold range for the data point's corresponding physiological metric based on the determined activity type.

In an embodiment, one or more stored lists comprising a listing of activity types may be accessed. Each of the activity types may have a corresponding listing of threshold ranges considered "normal" for each physiological metric. For example, a stored list may comprise a listing of activities such as sitting, walking, and running. The walking activity may be associated with additional threshold data that identifies that a normal heart rate for an average adult walking is between 80 to 120 BPM, a normal blood pressure is between 90/60 mmHg and 120/80 mmHg, etc. An average adult determined to be walking who has a detected heart rate of 110 BPM or detected blood pressure of 100/70 mmHg may be considered to operate in a normal range.

In an embodiment, the threshold ranges for each physiological metric may be further be adjusted based upon user-specific health considerations (e.g., age, weight, specific health condition, etc.). For instance, using the example in the previous paragraph, a highly trained adult athlete determined to be walking may output a heart rate of 70 BPM. Although this heart rate falls outside of the normal threshold range for an average adult walking (i.e., 80 to 120 BPM), due to the fitness level and above-average health of the athlete, their normal threshold walking range may be 60 to 100 BPM. An embodiment may support one or more user profiles (e.g., stored on a device, etc.) that may contain the user-specific health considerations and corresponding activity-based threshold ranges based on the user-specific health considerations. Additionally or alternatively, in an embodiment, the "normal" threshold ranges for one or more activity-based physiological metrics may be set and/or calibrated by a user. For example, a user may measure their heart beat, blood pressure, respiration levels, etc. while, or shortly after, performing an activity and record those results in the user profile. Alternatively, in another embodiment, these threshold ranges may be set by a manufacturer or programmer with reference to known normal "averages" of users at certain ages, certain body weights, having certain health conditions, etc.

Responsive to determining, at 304, that a physiological data point does not fall outside of a predetermined threshold range, an embodiment may, at 305, take no additional action. Conversely, responsive to determining, at 304, that a physiological data point does fall outside of a predetermined threshold range, an embodiment may, at 306, provide a notification to a user. In an embodiment, the notification may be an audible notification (e.g., audible message, alarm sound, etc.), visual notification (e.g., text box displayed on the screen, picture, animation, etc.), haptic notification (e.g., vibration of a user's device, etc.), a combination thereof, and the like. The notification may be provided using one or more output devices (e.g., speakers, display screens, haptic devices, etc.).

In an embodiment, the notification may be provided on a different device than a user's device. For example, a user may designate an "emergency contact" in their phone that an embodiment may automatically send a notification to responsive to determining that a physiological data point falls outside of a predetermined threshold for an activity. In the same vein, an embodiment may additionally or alternatively send the notification to a healthcare professional and/or an emergency service. For example, the notification may automatically be sent to a 911 number, a health care facility, a combination thereof, and the like.

An embodiment may additionally utilize physiological micro-event data in the determination of whether a notification should be provided to a user. In the context of this application, physiological micro-event data may refer to a physiological data point trend over a predetermined amount of time (e.g., the past 5 seconds, 30 seconds, 1 minute, etc.). More particularly, the physiological data point trend may refer to an activity level for a physiological metric An embodiment may identify whether one or more physiological data points in the trend are abnormally high or low with respect to the other points in the trend and/or identify whether one or more points in the trend fall outside of a threshold range for a current activity. Responsive to this identification, an embodiment may determine whether this abnormality is an expected result based upon the activity and/or additional context data. For example, if a user's heart rate suddenly increases by 20 BPM, an embodiment may determine whether this increase was expected or not. If a user was determined to be performing cardio circuits, an embodiment may recognize that periodic bursts in heart rate, even above a threshold range for the cardio circuit activity, should be expected based upon this activity and may therefore not provide a notification. Conversely, if an embodiment determines that a user is sleeping when these abnormal bursts occur, an embodiment may recognize that there is not a natural reason for these bursts to occur and may therefore provide a notification. An embodiment may also utilize additional context data to adjust the threshold range(s) for one or more physiological metrics based upon the expected activity levels that correspond with the context. For example, an embodiment may use location data to identify that a user is walking in an airport. An embodiment may recognize (e.g., by accessing a rules table, etc.) that a sudden burst in heart rate may be common in such a location (e.g., because individuals often increase their pace in order to catch a flight, etc.) and therefore not provide a notification.

Additional devices may also be used to obtain additional context data in the determination of whether to provide a notification. For instance, in the case of blood glucose monitoring, it is known that the type of food ingested has a different effect on the timing of blood glucose levels. By combining awareness of the food a user is consuming, an embodiment may provide additional confirmation input to a system that physiological data related to blood glucose levels falls within or outside of a threshold range. An embodiment may therefore utilize one or more cameras or devices (e.g., Snap Spectacles®, Google Clip®, etc.) to capture raw images of food intake for visual analysis and project, based on the identification of food types in those images, an anticipated trajectory of a user's blood glucose levels. For example, an embodiment may capture an image of a food item a user is consuming and analyze that image (e.g., using one or more image analysis techniques, etc.) to determine that a user has just eaten a candy bar. An embodiment may thereafter access a database comprising a listing of anticipated effects a particular food item may have on a user's blood glucose levels. In this case, an embodiment may identify that the consumption of a candy bar will likely raise a user's blood glucose levels relatively quickly. Therefore, utilizing this knowledge, an embodiment may implement a new "normal" threshold range, or adjust an existing threshold range, associated with a user's blood glucose levels to correspond with the anticipated spike in a user's blood glucose. If an embodiment identifies that a blood glucose measurement falls outside of this new or adjusted threshold range in the anticipated time frame, an embodiment may provide the notification. Additional methods may be used to identify a food a user has just consumed including, but not limited to, receiving manual user input, accessing a user's social media posts (e.g., pictures, comments, etc.), and the like.

The various embodiments described herein thus represent a technical improvement to conventional health-related notification techniques. Using the techniques described herein, an embodiment may obtain at least one physiological data point associated with a user (e.g., blood pressure, heart rate, blood glucose level, etc.). An embodiment may also determine an activity a user is currently engaging in (e.g., sitting, walking, running, etc.). An embodiment may thereafter determine whether a physiological data point falls outside of a threshold range for a corresponding physiological metric based on the activity type. Responsive to determining that the physiological data point falls outside of the threshold range, an embodiment may provide a notification to a user or another individual or service. Such techniques enable a device to provide more accurate notifications with respect to a user's health by considering a user's activity as well as by utilizing a variety of different types of context information.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, a system, apparatus, or device (e.g., an electronic, magnetic, optical, electromagnetic, infrared, or semiconductor system, apparatus, or device) or any suitable combination of the foregoing. More specific examples of a storage device/medium include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
   obtaining, at an information handling device, at least one physiological data point that corresponds to a physiological metric associated with a user;
   determining, using a processor, an activity type of the user, wherein the activity type corresponds to a scheduled task;
   determining, using the processor, whether the at least one physiological data point is outside a threshold range for the physiological metric based on the activity type, wherein the determining comprises:
      identifying a physiological data point trend over a predetermined period of time;
      identifying that at least one physiological data point in the physiological data point trend is aberrant to other data points in the physiological data point trend; and
      determining whether the aberrancy is expected based upon an expected activity level of the scheduled task; and
   providing, responsive to determining that the at least one physiological data point is outside the threshold range and using an output device integrally coupled to the information handling device, a notification that informs the user that the at least one physiological data point is outside the threshold range.

2. The method of claim 1, wherein the physiological metric is associated with at least one of the user's heart rate, blood pressure, respiration level, and blood glucose level.

3. The method of claim 1, wherein the determining the activity type comprises receiving context data associated with the user.

4. The method of claim 3, wherein the context data is selected from the group consisting of at least one of location data, movement data, communication data, social media data, and food consumption data.

5. The method of claim 3, wherein the context data is obtained from at least one other device.

6. The method of claim 3, wherein the physiological metric is associated with a user's blood glucose levels and wherein the context data is associated with the food consumption data and further comprising utilizing the food consumption data to identify an anticipated trajectory of the user's blood glucose levels.

7. The method of claim 6, further comprising adjusting the threshold range based on the anticipated trajectory.

8. The method of claim 3, wherein the determining the activity type comprises accessing a list of correlations between the received context data and activity types.

9. The method of claim 1, wherein the notification is provided to at least one of another device and another individual.

10. An information handling device, comprising:
    an output device;
    a processor;
    a memory device that stores instructions executable by the processor to:
    obtain at least one physiological data point that corresponds to a physiological metric associated with a user;
    determine an activity type of the user, wherein the activity type corresponds to a scheduled task;
    determine whether the at least one physiological data point is outside a threshold range for the physiological metric based on the activity type, wherein the instructions executable by the processor to determine whether the at least one physiological data point is outside the threshold range comprise instructions executable by the processor to:
       identify a physiological data point trend over a predetermined period of time;
       identify that at least one physiological data point in the physiological data point trend is aberrant to other data points in the physiological data point trend; and
       determine whether the aberrancy is expected based upon an expected activity level of the scheduled task; and
    provide, responsive to determining that the at least one physiological data point is outside the threshold range, a notification;
    providing, responsive to determining that the at least one physiological data point is outside the threshold range and using the output device, a notification that informs the user that the at least one physiological data point is outside the threshold range.

11. The information handling device of claim 10, wherein the physiological metric is associated with at least one of the user's heart rate, blood pressure, respiration level, and blood glucose level.

12. The information handling device of claim 10, wherein the instructions executable by the processor to determine the activity type comprise instructions executable by the processor to receive context data associated with the user.

13. The information handling device of claim 12, wherein the context data is selected from the group consisting of at least one of location data, movement data, communication data, social media data, and food consumption data.

14. The information handling device of claim 12, wherein the physiological metric is associated with a user's blood glucose levels and wherein the context data is associated with the food consumption data and wherein the instructions are further executable by a processor to utilize the food consumption data to identify an anticipated trajectory of the user's blood glucose levels.

15. The information handling device of claim 14, wherein the instructions are further executable by the processor to adjust the threshold range based on the anticipated trajectory.

16. The information handling device of claim 12, wherein the instructions executable by the processor to determine the activity type comprise instructions executable by the processor to access a list of correlations between the received context data and activity types.

17. The information handling device of claim 10, wherein the notification is provided to at least one of a remote device and another user.

18. A non-transitory computer readable storage medium having computer readable program code embodied therewith, the computer readable program code being executable by a processor and comprising:
  computer readable program code configured to obtain at least one physiological data point that corresponds to a physiological metric associated with a user;
  computer readable program code configured to determiner an activity type of the user, wherein the activity type corresponds to a scheduled task;
  computer readable program code configured to determine whether the at least one physiological data point is outside a threshold range for the physiological metric based on the activity type, wherein the computer readable program code configured to determine whether the at least one physiological data point is outside the threshold range comprises computer readable program code configured to:
    identify a physiological data point trend over a predetermined period of time;
    identify that at least one physiological data point in the physiological data point trend is aberrant to other data points in the physiological data point trend; and
    determine whether the aberrancy is expected based upon an expected activity level of the scheduled task; and
  computer readable program code configured to provide, using an output device and responsive to determining that the at least one physiological data point is outside the threshold range, a notification that informs the user that the at least one physiological data point is outside the threshold range.

* * * * *